(12) United States Patent
Brockman et al.

(10) Patent No.: US 10,932,839 B2
(45) Date of Patent: Mar. 2, 2021

(54) SYSTEMS AND METHODS FOR DELIVERING ELEMENTS WITHIN A FLUENT MATERIAL TO AN OFF-AXIS TARGET SITE WITHIN A BONE STRUCTURE

(71) Applicant: Stryker Corporation, Kalamazoo, MI (US)

(72) Inventors: Christopher Scott Brockman, Kalamazoo, MI (US); Matthew S. Emkow, Fishers, IN (US)

(73) Assignee: Stryker Corporation, Kalamazoo, MI (US)

( * ) Notice: Subject to any disclaimer, the term of this patent is extended or adjusted under 35 U.S.C. 154(b) by 78 days.

(21) Appl. No.: 16/224,303

(22) Filed: Dec. 18, 2018

(65) Prior Publication Data

US 2019/0183551 A1 Jun. 20, 2019

Related U.S. Application Data

(60) Provisional application No. 62/607,581, filed on Dec. 19, 2017.

(51) Int. Cl.
| | | |
|---|---|---|
| *A61B 17/88* | (2006.01) | |
| *A61B 17/70* | (2006.01) | |
| *A61B 17/00* | (2006.01) | |

(52) U.S. Cl.
CPC ...... *A61B 17/8816* (2013.01); *A61B 17/7094* (2013.01); *A61B 17/7095* (2013.01); *A61B 17/8811* (2013.01); *A61B 17/8819* (2013.01); *A61B 17/8855* (2013.01); *A61B 17/8827* (2013.01); *A61B 2017/00867* (2013.01)

(58) Field of Classification Search
CPC ............ A61B 17/8816; A61B 17/8811; A61B 17/7094; A61B 17/7095
See application file for complete search history.

(56) References Cited

U.S. PATENT DOCUMENTS

| | | | | |
|---|---|---|---|---|
| 3,805,776 A | * | 4/1974 | Thiele ................ | A61B 17/7061 606/60 |
| 4,820,306 A | * | 4/1989 | Gorman ............. | A61B 17/8816 128/898 |
| 6,048,346 A | * | 4/2000 | Reiley ................ | A61B 17/8811 606/83 |

(Continued)

*Primary Examiner* — Christian A Sevilla
(74) *Attorney, Agent, or Firm* — Howard & Howard Attorneys PLLC

(57) ABSTRACT

Systems and methods for stabilizing a bone structure of a patient. A stylet and a delivery tube is directed through an access cannula to form a curved path to a target site. The stylet is withdrawn with a distal portion of the flexible delivery tube maintaining a curved configuration along the curved path. The curable material including a plurality of elements disposed in a fluent material is directed through the flexible delivery tube with a distal portion of the flexible delivery tube maintaining the curved configuration against forces from the elements and the fluent material. A delivery cannula may be directed through the flexible delivery tube. An expandable member may deployed at the target site to create a cavity. A steerable assembly may be selectively activate to form the curved path. The plurality of elements may substantially follow a curved path created within the bone structure.

20 Claims, 9 Drawing Sheets

(56) References Cited

U.S. PATENT DOCUMENTS

| | | |
|---|---|---|
| 6,620,162 B2 | 9/2003 | Kuslich et al. |
| 8,226,657 B2 | 7/2012 | Linderman et al. |
| 8,894,658 B2 | 11/2014 | Linderman et al. |
| 9,301,792 B2 * | 4/2016 | Henniges ............ A61B 17/3472 |
| 10,022,173 B2 | 7/2018 | Linderman et al. |
| 10,881,520 B2 | 1/2021 | Messerli |
| 2002/0183761 A1 | 12/2002 | Johnson et al. |
| 2004/0097930 A1 | 5/2004 | Justis et al. |
| 2005/0278023 A1 | 12/2005 | Zwirkoski |
| 2006/0100304 A1 | 5/2006 | Vresilovic et al. |
| 2007/0093822 A1 | 4/2007 | Dutoit et al. |
| 2007/0162132 A1 | 7/2007 | Messerli |
| 2008/0294166 A1 * | 11/2008 | Goldin ............... A61B 17/1671 606/79 |
| 2013/0065002 A1 | 3/2013 | Nakashima et al. |
| 2013/0150831 A1 * | 6/2013 | Griffiths ................ A61B 17/29 606/1 |
| 2013/0345765 A1 | 12/2013 | Brockman et al. |
| 2016/0175019 A1 | 6/2016 | Henniges et al. |
| 2016/0228131 A1 | 8/2016 | Brockman et al. |
| 2018/0049772 A1 | 2/2018 | Brockman et al. |

\* cited by examiner

SYSTEMS AND METHODS FOR DELIVERING ELEMENTS WITHIN A FLUENT MATERIAL TO AN OFF-AXIS TARGET SITE WITHIN A BONE STRUCTURE

CROSS REFERENCE TO RELATED APPLICATION

This application claims priority to and all the benefits of U.S. Provisional Application No. 62/607,581, filed Dec. 19, 2017, the entire contents of which are hereby incorporated by reference.

BRIEF DESCRIPTION OF THE DRAWINGS

Advantages of the present invention will be readily appreciated as the same becomes better understood by reference to the following detailed description when considered in connection with the accompanying drawings.

DETAILED DESCRIPTION

Surgical intervention of a compromised bone, for example, a vertebral body, may be beneficially stabilized by the injection of a curable material such as a bone cement—a procedure known as a vertebroplasty. Prior to the injection of the curable material, a cavity may be created within the cancellous bone with the curable material being delivered into the cavity. A procedure known as a kyphoplasty includes creating the cavity by compressing the cancellous bone with an expandable member such as a balloon. The physician may desire more precise control of the curable material as the curable material interdigitates the cancellous bone and/or fills the created cavity. One solution disclosed in commonly owned United States Patent Publication No. 2016/0175019, filed Feb. 29, 2016, hereby incorporated by reference in its entirety, includes the curable material including a plurality of elements disposed with a fluent material. The elements may be designed and deployed in manner to optimize the packing characteristics of the implant and/or optimize delivery of the curable material at a target site in manners to be described.

Figure 3:
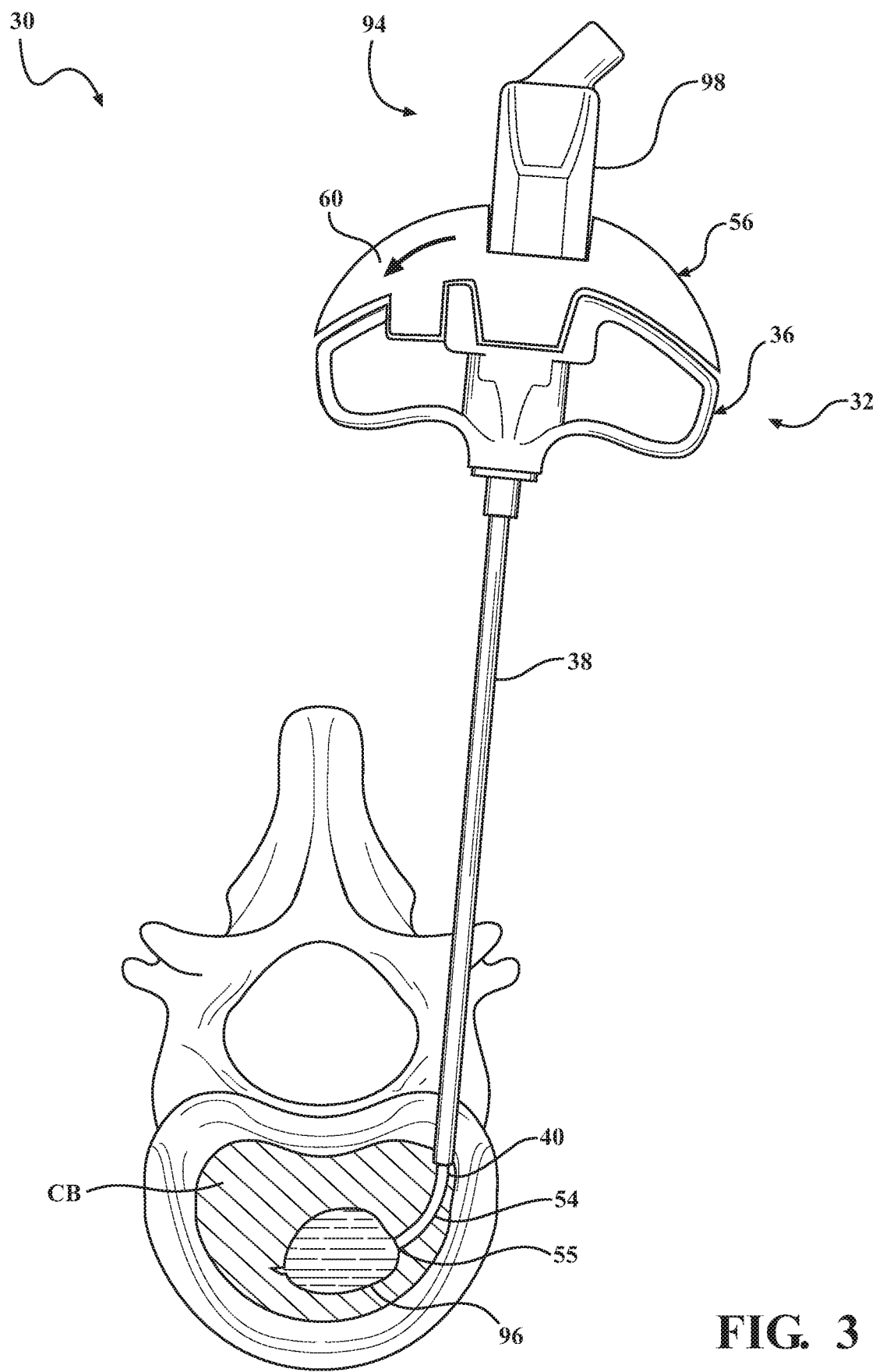
FIG. 3 shows a cavity-forming device including an expandable member in a deployed configuration creating a cavity at the target site.
Figure 4:
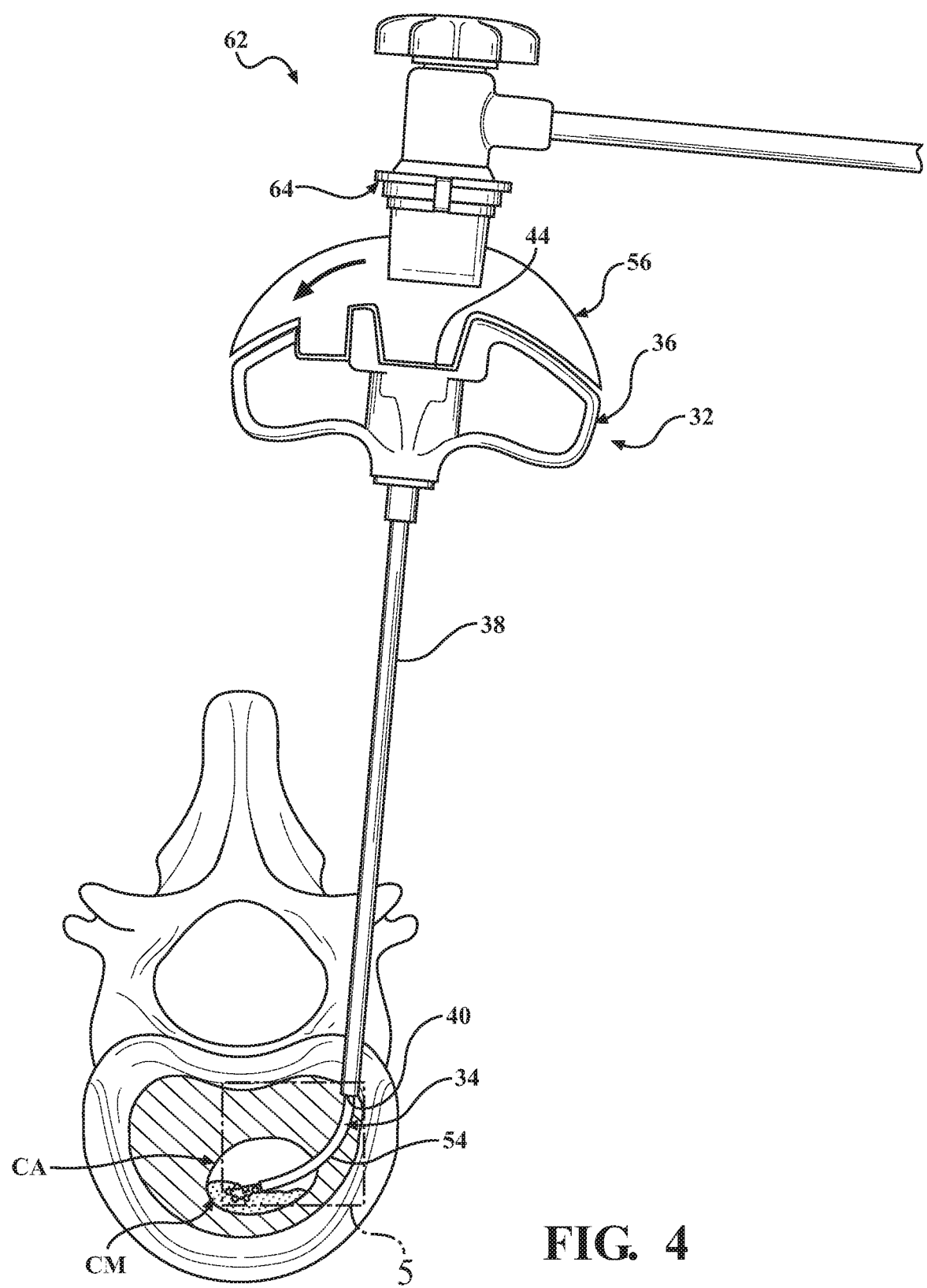
FIG. 4 shows a curable material delivery device directing curable material to the cavity created at the target site.
Figure 5:
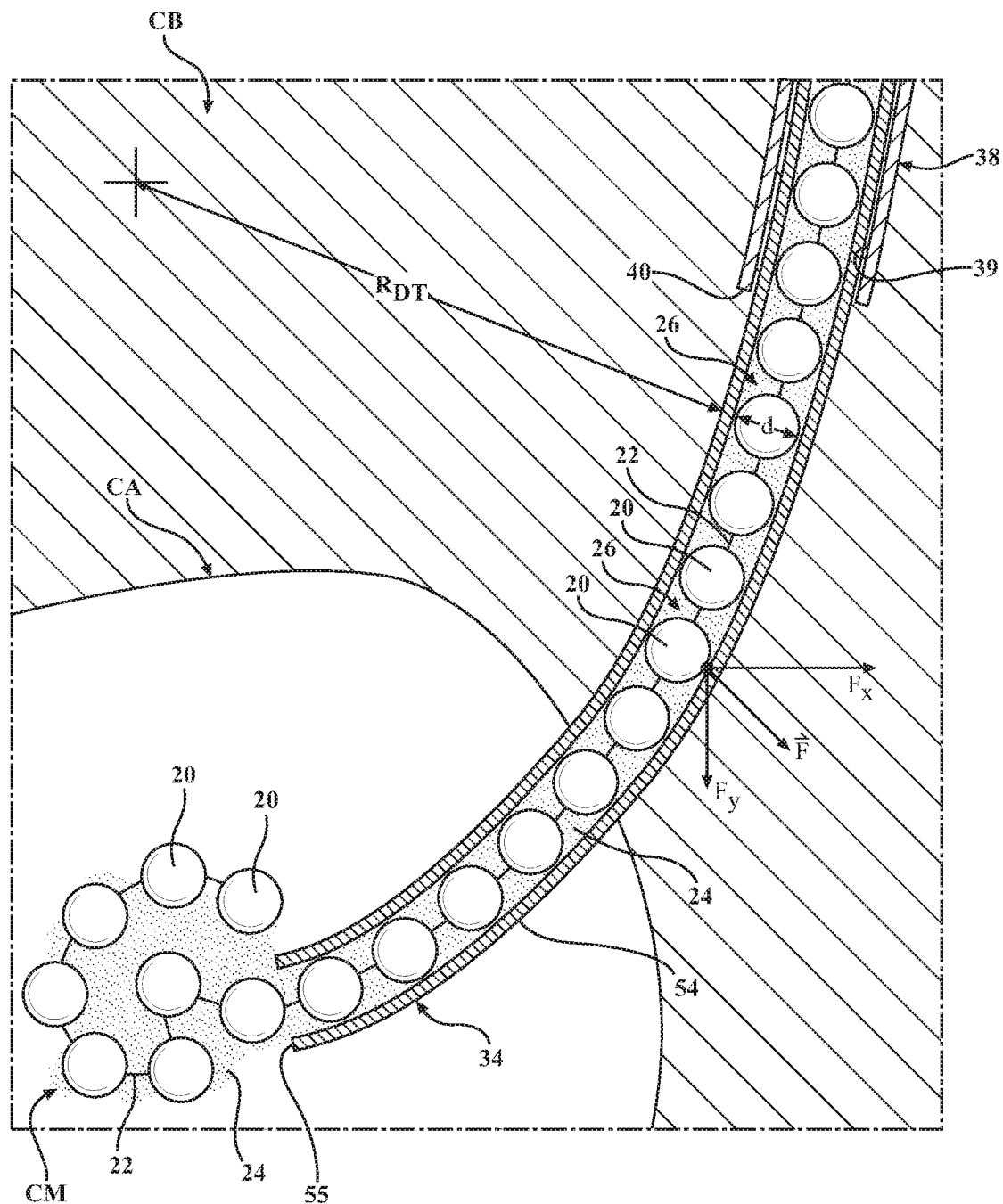
FIG. 5 is a detailed view of a portion of FIG. 4 within box 5-5 showing a distal portion of the flexible delivery tube directing the curable material including the elements within a fluent material to within the cavity.
Figure 6:
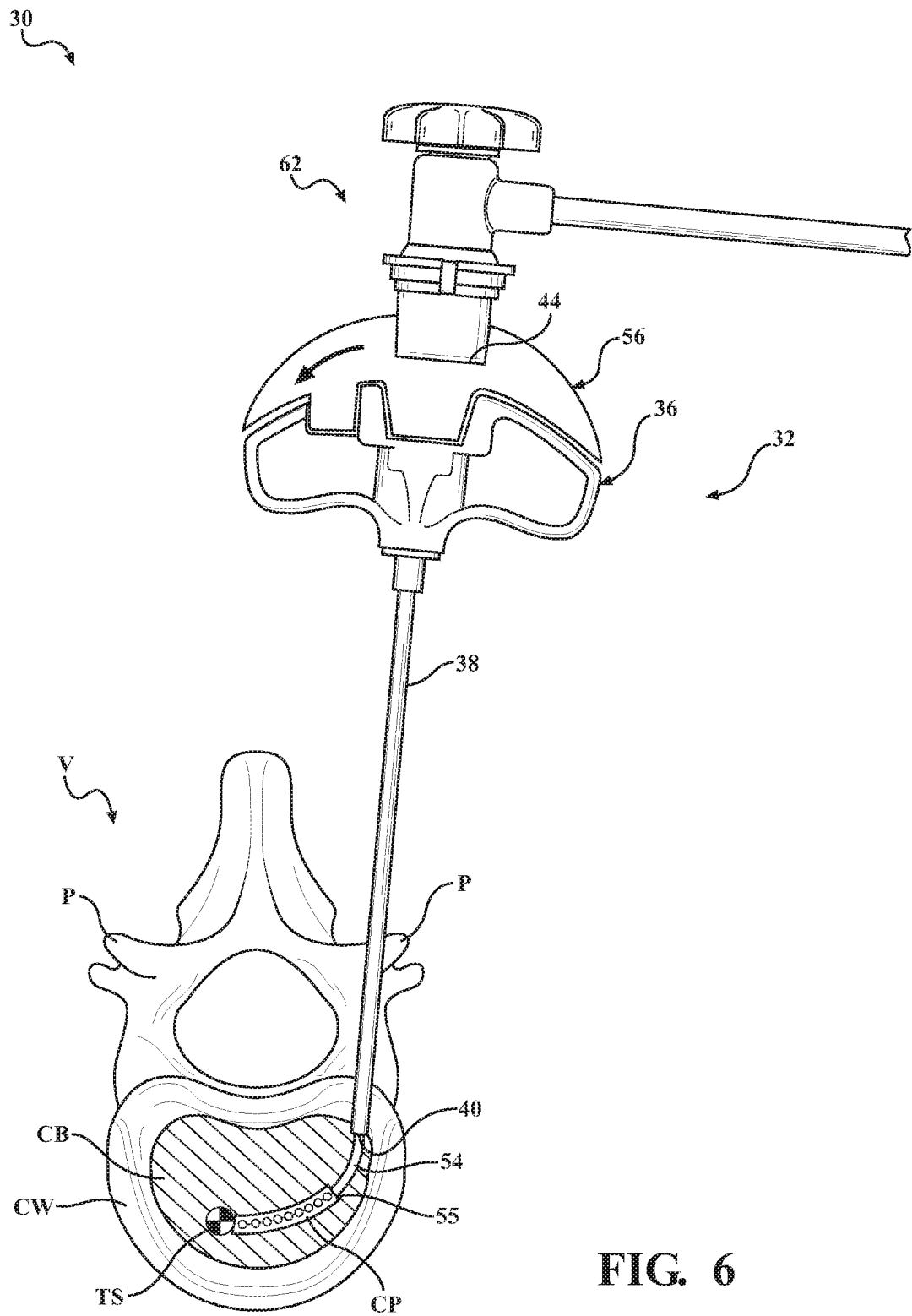
FIG. 6 shows the curable material delivery device directing the curable material to within a curved path within the bone structure.
Figure 7:
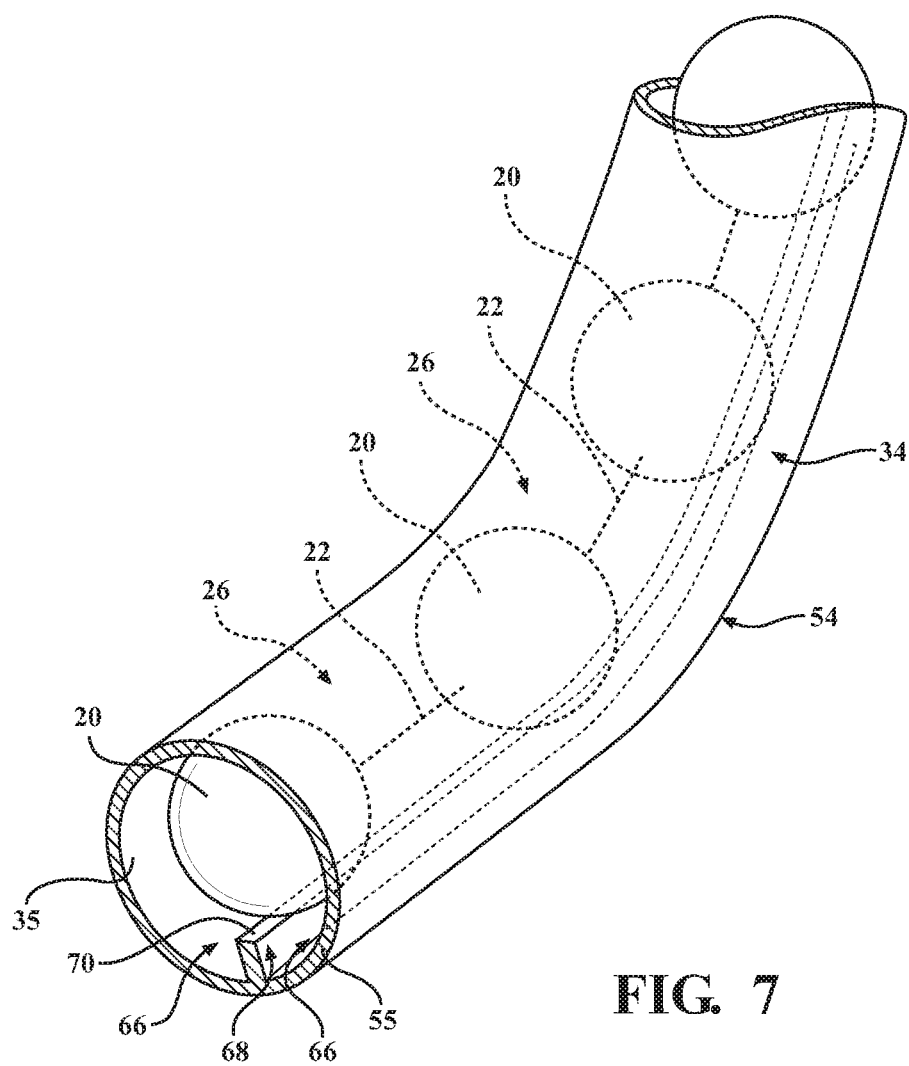
FIG. 7 is a perspective view of the distal portion of another flexible delivery tube.
Figure 8:
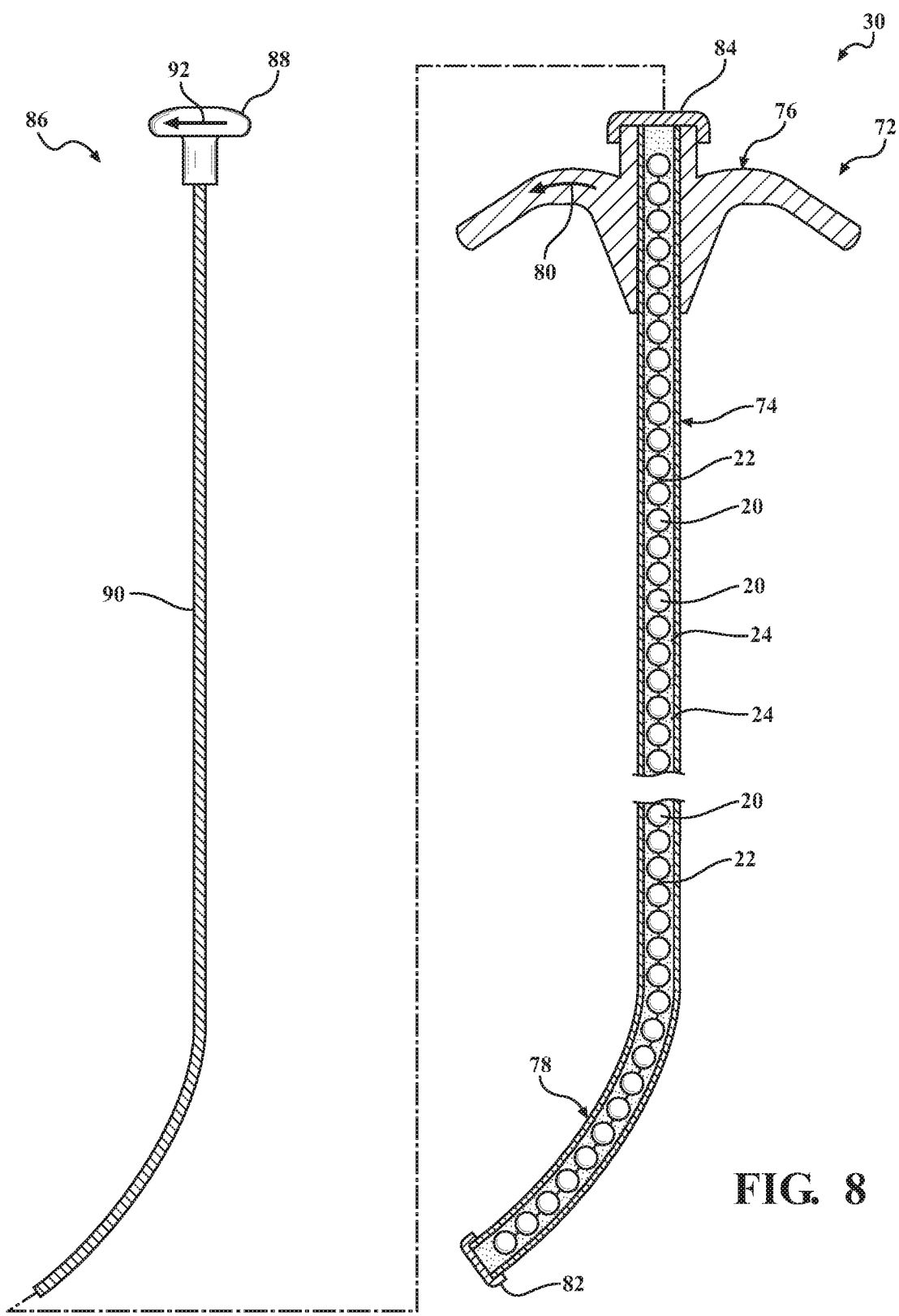
FIG. 8 is a plan view of a delivery cannula and a pushing device.

Referring to FIGS. 1-9 with like numerals indicating like components, the elements 20 may be interconnected by a connecting member 22, for example, a wire, string, fiber, or other suitable connector. The elements 20 may be loose within a fluent material 24 mixed with the elements 20. The elements 20 are solid in form, and may be formed of metals, alloys, ceramics, polymers, bone derived material, or combinations of these materials. The elements 20 may be bioabsorbable, non-bioabsorbable, radiopaque, radiolucent, and/or therapeutically-coated, among other characteristics. The elements 20 may include any shape (pellets, beads, oval-shaped, cylinder-shaped, faceted elements, box-shaped, dumb-bell shaped, nestled shapes, coils, etc.). FIGS. 5, 7 and 8 best show the elements 20 including a generally spherical shape and disposed adjacent to one another to form a linear array. Voids 26 may be defined between adjacent pairs of the elements 22. The fluent material 24 is preferably capable of setting to a hardened condition and is disposed within at least a portion of the voids 26. The fluent material 24 may be a slurry, liquid, paste, or gel that may solidify during or after delivery. In one example, the fluent material 24 is polymethylmethacrylate (PMMA).

Figure 1:
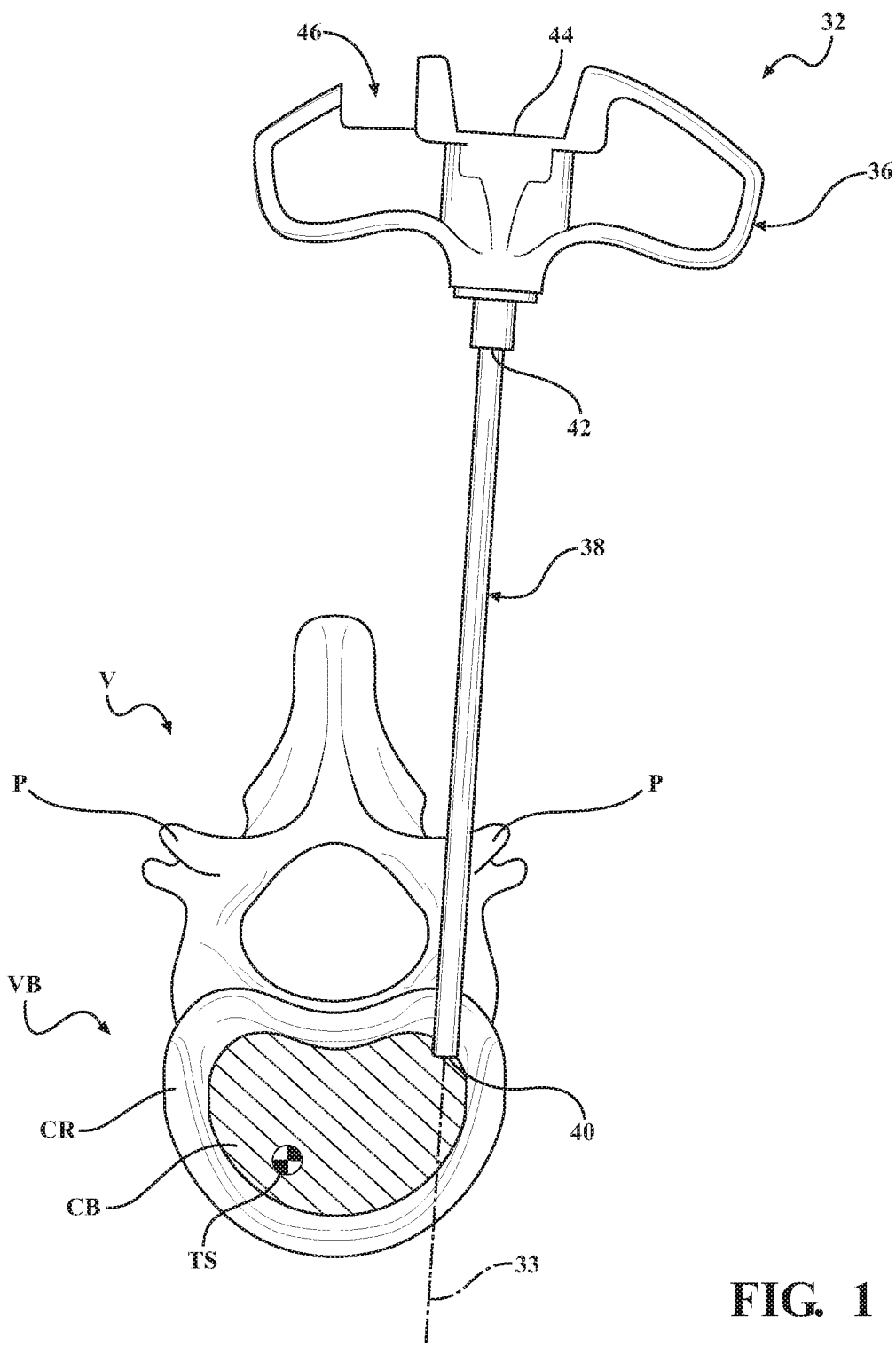
FIG. 1 is a schematic representation of an axial view of a vertebra with an access cannula of a vertebral augmentation system providing access to within the vertebral body of the vertebra.

FIG. 1 shows an axial view of a vertebra (V) with an access cannula 32 of a vertebral augmentation system 30 being directed through a pedicle (P) of the vertebral to provide access to a target site (TS). A vertebral body (VB) of the vertebra includes a cortical rim (CR) formed from cortical bone at least partially encapsulating a volume of cancellous bone (CB). The target site is within the cancellous bone at a location identified by the physician to be desirable to deploy curable material (CM) (see FIG. 5) to stabilize the vertebra. Certain vertebral augmentation procedures include accessing the target site with a bipedicular approach, wherein an access cannula is directed to each of the pedicles of the vertebra. One exemplary system utilizing the bipedicular approach is disclosed in commonly owned U.S. Pat. No. 8,226,657, issued Jul. 24, 2012, hereby incorporated by reference in its entirety. The instrumentation directed through the access cannulae to perform certain aspects of the procedure may be generally straight, as much of the interior of the vertebral body is accessible and such instrumentation is generally simpler in form and operation. Further, the delivery of the curable material including the elements 20 within the fluent material 24 follows a straight path within the instrumentation.

Of particular interest in the present application is a unipedicular approach, wherein the access cannula 32 is directed to one of the pedicles of the vertebra, as shown in FIG. 1. One exemplary system utilizing the unipedicular approach is disclosed in commonly owned U.S. Pat. No. 8,894,658, issued Nov. 25, 2014, hereby incorporated by reference in its entirety. The instrumentation associated with the unipedicular approach may provide for accessing locations of the interior of the vertebral body offset from a longitudinal axis 33 of the access cannula 32 (see FIG. 1), for example a curved path provided by a flexible delivery tube 34 to a contralateral side of the vertebral body (VB). It is readily appreciated that the off-axis delivery of the curable material is associated with technical challenges, as the curable material may need to follow the curved path to the target site. These challenges may be considered especially pronounced in systems where the curable material includes the elements 20 within the fluent material 24; e.g., the elements 20 impart appreciable forces to the flexible delivery tube 34 or other device that provides the curved path. The system 30 of the present disclosure overcomes these challenges in manners to be explained in greater detail.

With continued reference to FIG. 1 and further reference to FIGS. 2-5, the system 30 includes the access cannula 32. The access cannula 32 includes a handle 36 for manipulating the access cannula 32, and a shaft 38 extending distally from the handle 36. The shaft 38 defines a lumen 39 extending between a distal end 40 opposite a proximal end 42 coupled to the handle 36 as shown in FIG. 1. The shaft 38 is generally straight such that the lumen 39 is oriented on or defines the longitudinal axis 33. The handle 36 includes an opening (not shown) in communication with the lumen 39 of the shaft 38 to allow various instrumentation such as the flexible delivery tube 34, among others to be described, to pass therethrough. A suitable connector 44 and orientation feature 46 may be provided on the handle 36 to facilitate removable engagement of the instrumentation with the access cannula 32.

As mentioned, the access cannula 32 is directed to one of the pedicles of the vertebra to provide access to the target site. More particularly, a trocar (not shown) with a pointed tip may be slidably and removably disposed within the lumen 39 of the shaft 38 such that the pointed tip is generally in registration with the distal end 40 of the access cannula 32. The trocar pierces the pedicle, and the distal end 40 of the access cannula 32 is positioned within the interior of the vertebral body near the target site, for example just beyond the cortical wall as shown in FIG. 1. The trocar is removed, and the lumen 39 of the access cannula 32 provides a working channel for the remainder of the procedure.

Figure 2:
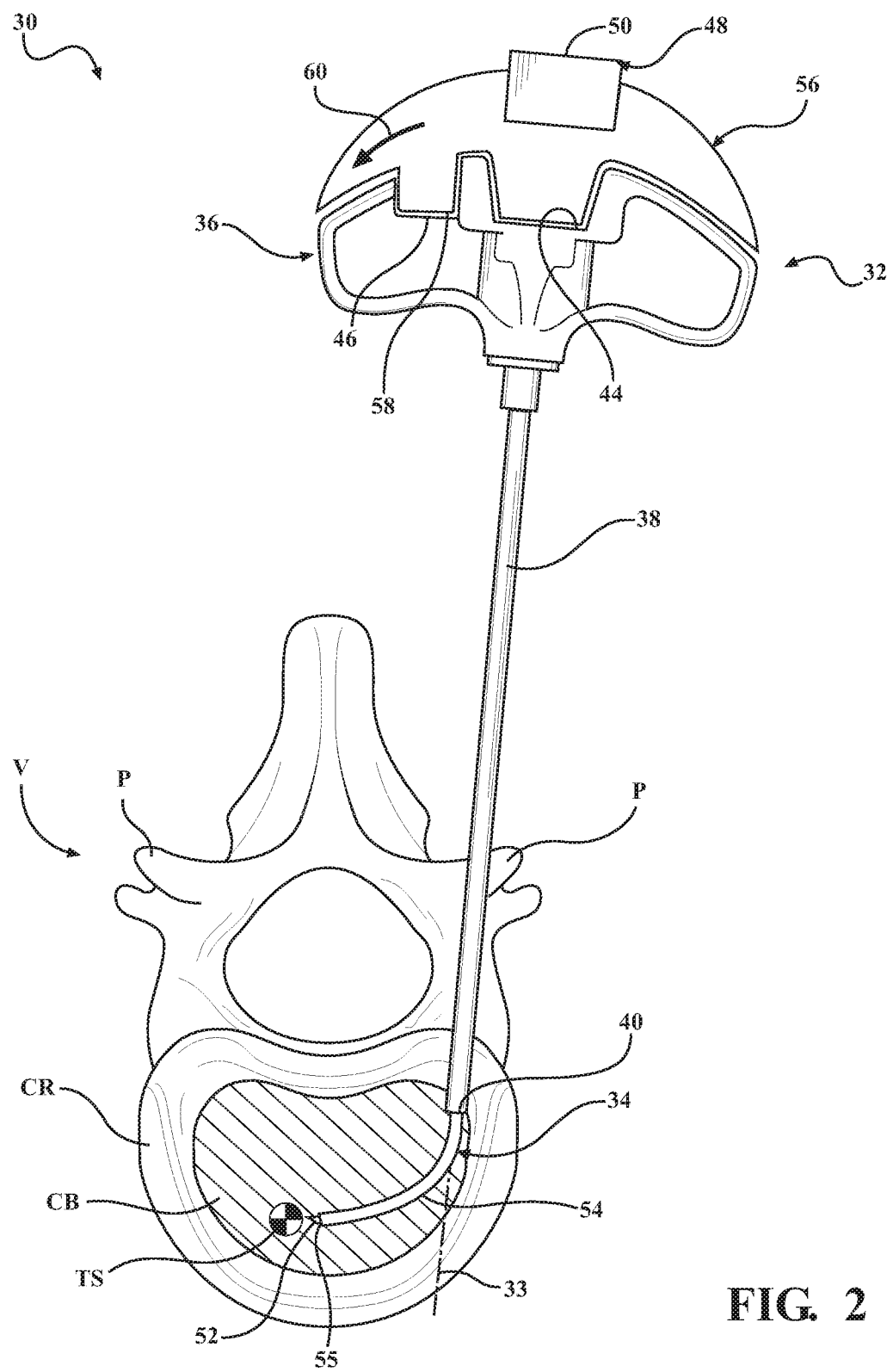
FIG. 2 shows a stylet and flexible delivery tube of the vertebral augmentation system forming a curved path to a target site within the vertebral body.

With reference to FIG. 2, a stylet 48 and the flexible delivery tube 34 may be provided and directed through the lumen 39 of the access cannula 32. The stylet 48 may include a handle 50 and a shaft extending distally from the handle 50. A distal portion (not identified) including a distal end 52 of the shaft may include a pre-set curve formed from memory metal (e.g., Nitinol) such that, the pre-set distal curved portion of the stylet 48 is held generally longitudinally straight (i.e., on the longitudinal axis 33) when directed through and constrained by the access cannula 32. The stylet 48 includes an outer diameter sized to be snugly and slidably disposed within an inner diameter of the flexible delivery tube 34 such that the flexible delivery tube 34 overlies the stylet 48. The distal end 52 of the stylet 48 may generally be in registration with a distal end 55 of the flexible delivery tube 34. Further, the flexible delivery tube 34 includes an outer diameter sized to be snugly and slidably disposed within an inner diameter of the lumen 39 of the access cannula 32, and each of the flexible delivery tube 34 and the stylet 48 have a length sufficient to extend through and be operable beyond the distal end 40 of the access cannula 32. As a result, as the stylet 48 and the flexible delivery tube 34 are simultaneously and coaxially directed through the access cannula 32 such that the pre-set distal curved portion, no longer constrained by the access cannula 32, forms a curved path to the target site as it is extended out of the distal end 40 of the access cannula 32, as shown in FIG. 2. In other words, the shape memory returns to its natural state, and the flexible delivery tube 34 owing to its relative flexibility is deformed to a shape complementary to the natural state of the pre-set distal curved portion of the stylet 48.

With continued reference to FIG. 2, the flexible delivery tube 34, a handle 56 may be coupled at a proximal end of the flexible delivery tube 34. The handle 56 may include an orientation feature 58 complementary to the orientation feature 46 of the handle 36 of the access cannula 32. Further, indicia 60 may be disposed on the handle 56 coupled to the flexible delivery tube 34. As such, with the flexible delivery tube 34 coupled to and oriented relative to the stylet 48 with the pre-set curved distal portion configured to deflect in a single direction (i.e., its natural state), the indicia 60 provides visual information to the physician as to a direction of the curved path once the stylet 48 and delivery tube 34 are no longer constrained by the access cannula 32. The complementary orientation features 46, 48 may engage to ensure the flexible delivery tube 34 with its distal portion 54 in a curved configuration in a single direction, remains fixed relative to the access cannula 32 secured within the bone structure.

The stylet 48 is withdrawn from the flexible delivery tube 34. The distal portion 54 of the flexible delivery tube 34 maintains the curved configuration along the curved path within the bone structure. At least the distal portion 54 of the flexible delivery tube 34 may be formed from materials striking an appropriate balance between flexibility (relative to the forces exerted by the pre-set distal curved portion of the stylet 48) and stiffness to maintain the curved configuration within the vertebral body. The cancellous bone surrounding the distal portion 54 of the flexible delivery tube 34 may facilitate the maintaining of the curved configuration as well.

Referring now to FIGS. 4 and 5, the curable material (CM) is directed through the flexible delivery tube 34 to the target site with the distal portion 54 of the flexible delivery tube 34 maintaining the curved configuration as the elements 20 disposed in the fluent material 24 are directed through the distal portion 54 of the flexible delivery tube 34. FIG. 4 shows a curable material delivery system 62 coupled to the handle 36 of the access cannula 32. The curable material delivery system 62 may include a hub 64 configured to removably couple with the connector 44 of the handle 36. The curable material delivery system 62 is in communication with a source of curable material (not shown). The curable material delivery system 62 may supply pressure to direct the curable material through the flexible delivery tube 34 and to the target site.

Owing to the solid or semi-solid form of the elements 20, the elements 20 may impart appreciable forces to the flexible delivery tube 34, as previously mentioned. Whereas FIG. 5 may exaggerate the voids 26 between the elements 20, the elements 20 may be nestled close together and include an outer dimension slightly less than the inner diameter of the distal portion 54 of the flexible delivery tube 34. The forces provided by the curable material delivery system 62 (or a pushing device 86 to be described) to the proximal-most element 20 must be effectively transferred in series along the linear array of the elements 20 along with the fluent material 24 disposed within the voids 26. The result may include forces generally against the direction of the curved path; e.g., force vectors normal to the distal portion 54 at respective locations with one such vector identified in FIG. 5. The force vector, or at least one or more of its component forces, may urge the distal portion 54 of the flexible delivery tube 34 to tend to straighten within the bone structure. It is appreciated that such forces may be significantly less considerable in applications where only the curable material (i.e., with no elements), in its fluent form, is directed along the curved path.

The system 30 of the present disclosure advantageously facilitates the off-axis delivery of the curable material including the elements 20 within the fluent material 24. The distal portion 54 of the flexible delivery tube 34 may be formed from a flexible polymer having sufficient columnar strength to maintain a patent longitudinal lumen and maintain the curved configuration against forces from the elements 20. Additionally or alternatively, the flexible delivery tube 34 may include stiffening structures (not shown) that are configured to maintain the curved configuration. Exemplary stiffening structures may include ribs, wires, coils, and the like, coupled to or otherwise associated with the distal portion 54 to provide additional stiffness to the distal portion 54 (and still permit the distal portion 54 to be deformed by the pre-set curved portion of the stylet 48).

The reduction of pressurization of the fluent material 24 may correspondingly reduce the forces on the distal portion 54 of the flexible delivery tube 34, and thereby facilitate maintaining the curved configuration against forces from the elements 20 being directed there through. An inner diameter of the flexible delivery tube 34 along the distal portion 54 in the curved configuration may be greater than the outer dimensions of the elements 20. As the curable material is directed through the distal portion 54 in the curved configuration, the fluent material 24 backflows through or between voids 26 between the elements 20. With continued reference to FIG. 5, the elements 20 may include an outer dimension, d, slightly less than the inner diameter of the flexible delivery tube 34 along the distal portion 54. A gap may be provided between the outer surface of the elements 20 and the inner surface of the flexible delivery tube 34 with the voids 26 between adjacent pairs of the elements 20 being in communication. The outer dimension, d, may be sized based on the viscosity of the fluent material 24 to permit adequate backflow of the same. Additionally or alternatively, the outer dimension, d, may be sized based on a magnitude of the curvature and/or a radius of curvature ($R_{ST}$) of the flexible delivery tube 34. In other words, the "straightening" forces from the elements 20 may be greater with the flexible delivery tube 34 curved to, for example, 90 degrees than to a less amount, and permitting for greater backflow at the greater curvature may reduce the forces. In still other variants, the elements 20 may be asymmetrically shaped, for example as disclosed in the aforementioned United States Patent Publication No. 2016/0175019, thereby permitting the fluent material 24 to backflow through or between voids 26 between the elements 20.

Referring now to FIG. 7, at least the distal portion 54 of the flexible delivery tube 34 may include at least one groove 66 extending longitudinally within the lumen 35 of the flexible delivery tube 34. The groove 66, in a most general sense, provides a pathway from the backflow of the fluent material 24 to reduce pressurization during deploying of the curable material from the flexible delivery tube 34 to the target site. FIG. 7 shows a rail 68 extending longitudinally along the lumen 35 of the flexible delivery tube 34 to define the groove 66 on each side of the rail 68. More particularly, the rail 68 extends radially inwardly from the flexible delivery tube 34 into the lumen 35, and the elements 20 include an outer dimension (e.g., d) sized to be snugly and slidably moved between a portion of the lumen 35 and an upper surface 70 of the rail 68. The grooves 66 on each side of the rail 68 include a dimension at least equal to a height of the rail 68 to permit the backflow of the fluent material 24 within the grooves 66. Other suitable configurations for the groove(s) 66 are contemplated, for example those disclosed in the aforementioned United States Patent Publication No. 2016/0175019.

The grooves 66 are preferably positioned along an outer side of the flexible delivery tube 34 relative to the direction of the curve of the distal portion 54. FIG. 7 shows the direction of curve generally defining an inner side opposite the outer side. The rail 68 extends longitudinally within the lumen 35 along the outer side. As the fluent material 24 may have a tendency to move along the outer side of the distal portion 54, and positioning the grooves 66 along the outer side (with the elements 20 being constrained by the rail 68) may facilitate improved backflow of the fluent material 24 to reduce pressurization.

As previously mentioned, the curable material delivery system 62 in communication with a source of curable material may supply pressure to direct the curable material through the flexible delivery tube 34 and to the target site. Referring now to FIG. 8, a delivery device 72 may be provided with the delivery device 72 including a delivery cannula 74, and a handle 76 coupled to the delivery cannula 74 for manipulating the delivery device 72. The delivery cannula 74 may be pre-loaded with the curable material including the elements 20 within the fluent material 24, as shown in FIG. 8. With the fluent material 24 pre-loaded, one or more retention caps 82, 84 may be removably coupled to the delivery device 72 to selectively cover proximal and distal ends of the delivery cannula 74. The delivery cannula 74 is may be directed through the flexible delivery tube 34. The delivery cannula 74 may include a flexible portion 78 that is configured to generally track the distal portion 54 of the flexible delivery tube 34 in the curved configuration. The distal portion 54 of the flexible delivery tube 34 is sufficiently stiff, in manners previously described, to maintain the curved configuration as the flexible portion 78 of the delivery cannula 74 is directed through the distal portion 54 of the flexible delivery tube 34.

The flexible portion 78 of the delivery cannula 74 may be formed from flexible material, for example a polymer, to omnidirectionally deflect based on the direction of the bend of the distal portion 54 of the flexible delivery tube 34. In one variant, the flexible portion 78 of the delivery cannula 74 may constructed to bend or flex in a single direction. In such a variant, the delivery device 72 may include indicia 80 indicative of the single direction of bend or flex such that the physician may register the single direction of bend of the flexible portion 78 with the single direction of the bend of the distal portion 54. In other words, the physician may align the indicia 80 on the handle 76 of the delivery device 72 with the indicia 60 on the handle 50 coupled to the flexible delivery tube 34. The retention cap 82 at the distal end of the delivery cannula 74 may be removed prior to directing the delivery cannula 74 through the flexible delivery tube 34.

The curable material may be directed through and out of the delivery cannula 74 to the target site. The system 30 may include the pushing device 86 including a handle 88 and a flexible shaft 90 extending distally from the handle 88. The pushing device 86 includes an outer diameter sized to be snugly and slidably disposed within an inner diameter of the delivery cannula 74. The flexible shaft 90 of the delivery cannula 74 may be formed from flexible material, for example a polymer or metal, to omnidirectionally deflect based on the direction of the bend of the distal portion 54 of the flexible delivery tube 34 (and/or the flexible portion 78 of the delivery cannula 74). In one variant, the flexible shaft 90 may constructed to bend or flex in a single direction, and the pushing device 86 may include indicia 92 indicative of the single direction of bend or flex such that the physician may register the single direction of bend of the flexible shaft 90 with the single direction of the bend of the distal portion 54 (and/or the flexible portion 78). The retention cap 84 at the proximal end of the delivery cannula 74 may be removed prior to or after directing the pushing device 86 through the delivery cannula 74. When fully inserted, a distal end of the pushing device 90 may generally be in registration with a distal end 55 the delivery cannula 74. A plunger (not shown)

may be disposed at the distal end of the pushing device 86. Certain features of the pushing device 86 for pressure reduction and the like are disclosed in the aforementioned United States Patent Publication No. 2016/0175019. It is further contemplated that the pushing device 86 may be directed through the flexible delivery tube 34 (i.e., without the use of the delivery device 74). In such an arrangement, the pushing device 86 directs the curable material through the flexible delivery tube 34 with the pushing device 86 being flexible to follow the distal portion 54 of the flexible delivery tube 34, and the distal portion 54 of the flexible delivery tube 34 maintain the curved configuration.

The above disclosure has generally been directed to the vertebroplasty augmentation procedure, wherein the curable material is directed into and interdigitated with the cancellous bone within the vertebral body. As mentioned, it may be desirable to perform a kyphoplasty procedure including compressing the cancellous bone and create a cavity for receiving the curable material. With reference to FIG. 3, the system 30 may include a cavity-forming device 94 including an elongate body (not shown) and an expandable member 96 at a working end. In one example, the expandable member is a balloon. The elongate body and the expandable member 96 are sized to be slidably directed through the lumen 35 of the flexible delivery tube 34. The cavity-forming device 94 may include a hub 98 configured to removably couple with the connector 44 of the handle 36 (and/or the handle 50 of the flexible delivery tube 34). As the expandable member 96 is directed through the lumen 35 of the flexible delivery tube 34, the distal portion 54 of the flexible delivery tube 34 maintaining the curved configuration in manners previously described. FIG. 5 shows the expandable member 96 directed out of the distal end 55 of the flexible delivery tube 34 at the target site.

The expandable member 96 is configured to be arranged in fluid communication with a fluid source (not shown) for selectively moving between a contracted configuration in which an absence of fluid permits the passage of the expandable member 96 through the flexible delivery tube 34, and a deployed configuration in which the presence of fluid expands the expandable member 96 to compress or compact the cancellous bone and form a cavity (CA) at the target site (see FIGS. 4 and 5). Certain structural properties and features of the expandable member 96 are disclosed in the aforementioned U.S. Pat. No. 8,226,657. The curable material including the elements 20 within the fluent material 24 is directed through the flexible delivery tube 34 to within the cavity formed by the expandable member 96, as best shown in FIG. 5.

It is contemplated that the cavity may be formed with a curette, for example the devices disclosed in commonly owned United States Patent Publication No. 2016/0228131, filed Apr. 13, 2016, hereby incorporated by reference in its entirety, and/or with another stylet (not shown) with a length to be extended beyond the distal end 55 of the flexible delivery tube 34 and manipulated in a manner to displace the cancellous bone and create the cavity (e.g., reciprocal and/or rotation motion).

In another exemplary method, prior to the step of directing the curable material into the bone structure, the flexible delivery tube 34 is at least partially retracted, thereby revealing or otherwise providing a curved path (CP) within the bone structure (e.g., an arcuate channel defined by the cancellous bone). With reference to FIG. 6, the distal end 55 is moved proximally towards the distal end 40 of the access cannula 32 through suitable controls on at least one of the handles 36, 56. The curable material is directed through the flexible delivery tube 34 to the target site, and the distal portion 54 of the flexible delivery tube 34 maintains the curved configuration. Once exiting the distal end 55 of the flexible delivery tube 34, the elements 20 (and the fluent material 24) substantially follow the curved path (CP) of the bone structure created by the retracted flexible delivery tube 34. The cavity-forming device 94 may be directed through the flexible delivery tube 34 such that the expandable member 96 is positioned within or otherwise follows the curved path within the bone structure distal to the distal end 55 of the flexible delivery tube 34, for example as disclosed in commonly owned U.S. Pat. No. 10,022,173, issued Jul. 17, 2018, hereby incorporated by reference in its entirety. The expandable member 96 is moved to the deployed configuration to create the cavity, and the curable material including the elements 20 within the fluent material 24 is directed through the flexible delivery tube 34 to within the cavity.

Figure 9:
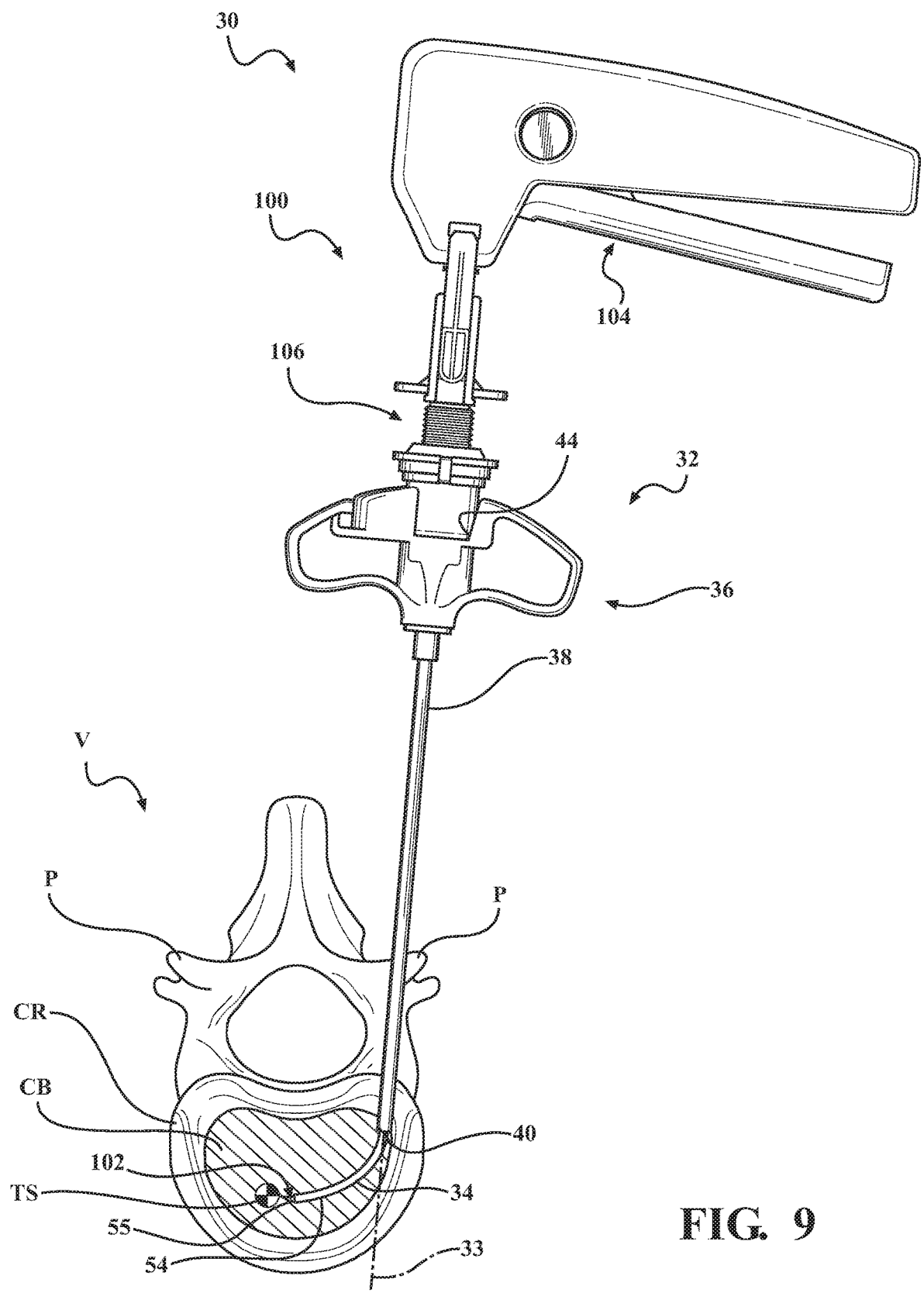
FIG. 9 shows a steerable assembly and the flexible delivery tube of the vertebral augmentation system.

Referring now to FIG. 9, the system 30 includes the access cannula 32 and further may include a steerable assembly 100 including a steering instrument 102, and the flexible delivery tube 34. The steering instrument 102 extends through the flexible delivery tube 34. The steerable assembly 100 includes a deflection mechanism (not shown) coupled at or near a distal end of the steering instrument 102, and an actuator 104 operably coupled to the deflection mechanism. An exemplary arrangement of the steerable assembly 100 is disclosed in commonly owned United States Patent Publication No. 2018/0049772, filed Feb. 22, 2018, hereby incorporated by reference in its entirety.

The steering instrument 102 is directed through the access cannula 32. The steerable assembly 100 may include a hub 106 configured to removably couple with the connector 44 of the handle 36, as shown in FIG. 9. The actuator 106 is actuated (e.g., the trigger is engaged) to activate the steering instrument 102 such that a portion of the steering instrument 102 positioned beyond the distal end 40 of the access cannula 32 forms a curved path to the target site (TS). The flexible delivery tube 34 overlying the steering instrument 102 and extending beyond the distal end 40 of the access cannula 32 is correspondingly deformed in manners previously described, and the distal portion 54 of the flexible delivery tube 34 assumes a curved configuration on the curved path. The actuator 106 may again be actuated to effectively deactivate the steering instrument 102 such that the distal end the steering instrument is adapted to relaxes and flex freely in an unrestrained mode. In the unrestrained mode, retraction of the distal end of the steering instrument 102 is permitted from the flexible delivery tube 34 with the distal portion 54 maintaining the curved configuration along the curved path within the bone structure to the target site. The steering instrument 102 is withdrawn from the flexible delivery tube 34, and in manners previously described the curable material including the elements 20 disposed in the fluent material 24 is directed through the distal portion 54 of the flexible delivery tube 34 without substantially displacing the distal portion of the flexible delivery tube 34 from the curved configuration. Certain features (e.g., backflow for pressure reduction, the curable material delivery system 62, the delivery cannula 72, the pushing device 86, the cavity-forming device 94, curved path in bone structure, etc.) are omitted in the interest of brevity and are hereby incorporated by reference. Again, the system 30 advantageously facilitates the off-axis delivery of the curable material including the elements 20 within the fluent material 24 and overcomes the technical challenges associated with the same.

The foregoing description is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method for stabilizing a bone structure of a patient with a curable material including a plurality of elements disposed in a fluent material, said method comprising the steps of:
    directing a distal end of an access cannula having a longitudinal axis into the bone structure near a target site;
    providing a stylet including a pre-set distal curved portion including memory metal, and a flexible delivery tube through which the stylet snugly and slidably extends, wherein the stylet and the flexible delivery tube are held generally longitudinally straight when constrained by the access cannula and have sufficient length to extend through and be operable beyond the distal end of the access cannula;
    directing the stylet and the flexible delivery tube simultaneously and coaxially through the access cannula such that the pre-set distal curved portion, no longer constrained by the access cannula, forms a curved path to the target site as it is extended out of the distal end of the access cannula;
    withdrawing the stylet from the flexible delivery tube with a distal portion of the flexible delivery tube maintaining a curved configuration along the curved path within the bone structure to the target site; and
    directing the curable material through the flexible delivery tube to the target site with the distal portion of the flexible delivery tube maintaining the curved configuration as the plurality of elements disposed in the fluent material are directed through the distal portion of the flexible delivery tube.

2. The method of claim 1, further comprising the steps of:
    directing a delivery cannula of a delivery device through the flexible delivery tube with the distal portion of the flexible delivery tube maintaining the curved configuration as a flexible portion of the delivery cannula is directed through the distal portion of the flexible delivery tube; and
    directing the curable material through the delivery cannula to the target site.

3. The method of claim 2, further comprising the step of pre-loading the delivery device with the curable material prior to directing the delivery cannula of the delivery device through the flexible delivery tube.

4. The method of claim 1, further comprising the steps of:
    directing a cavity-forming device including an expandable member through the flexible delivery tube to the target site within the bone structure with the distal portion of the flexible delivery tube maintaining the curved configuration as the expandable member is directed through the distal portion of the flexible delivery tube; and
    forming a cavity with the expandable member of the cavity-forming device at the target site.

5. The method of claim 4, wherein the curable material is directed through the flexible delivery tube to within the cavity.

6. The method of claim 1, wherein the distal portion of the flexible delivery tube is formed from a flexible polymer having sufficient columnar strength to maintain a patent longitudinal lumen and the curved configuration against tangential forces from the plurality of elements being directed through the distal portion of the flexible delivery tube.

7. The method of claim 6, wherein an inner diameter of the flexible delivery tube along the distal portion in the curved configuration is greater than outer dimensions of the plurality of elements such that, as the curable material is directed through the distal portion in the curved configuration to the target site, the fluent material backflows through voids between the plurality of elements and the flexible delivery tube to reduce pressurization of the fluent material.

8. The method of claim 1, wherein the flexible delivery tube includes at least one groove extending longitudinally along an outer side of the distal portion in the curved configuration such that, as the curable material is directed through the distal portion in the curved configuration to the target site, the fluent material backflows within the groove to reduce pressurization of the fluent material.

9. The method of claim 1, further comprising the step of directing a pushing device through the flexible delivery tube to direct the curable material through the flexible delivery tube to the target site, wherein the pushing device is flexible to follow the distal portion of the flexible delivery tube maintained the curved configuration.

10. A method for stabilizing a bone structure of a patient with a curable material including a plurality of elements disposed in a fluent material, said method comprising the steps of:
    directing a distal end of an access cannula having a longitudinal axis into the bone structure near a target site;
    providing a steerable assembly including a steering instrument and a flexible delivery tube through which the steering instrument slidably extends, wherein the steerable assembly includes a deflection mechanism coupled near a distal end of the steering instrument, the method comprising:
    directing the steering instrument through the access cannula;
    activating the steering instrument such that a portion of the steering instrument positioned beyond the distal end of the access cannula forms a curved path to the target site;
    withdrawing the steering instrument from the flexible delivery tube, wherein the distal end of the steering instrument is adapted to relax and flex freely in an unrestrained mode to permit retracting of the distal end of the steering instrument from the flexible delivery tube maintaining a curved configuration along the curved path within the bone structure; and
    directing the curable material through the flexible delivery tube to the target site without substantially displacing the distal portion of the flexible delivery tube from the curved configuration as the plurality of elements disposed in the fluent material are directed through the distal portion of the flexible delivery tube.

11. The method of claim 10, further comprising the steps of:
    directing a delivery cannula of a delivery device through the flexible delivery tube with the distal portion of the flexible delivery tube maintaining the curved configuration as a flexible portion of the delivery cannula is directed through the distal portion of the flexible delivery tube; and directing the curable material through the delivery cannula to the target site.

12. The method of claim 11, further comprising the step of pre-loading the delivery device with the curable material prior to directing the delivery cannula of the delivery device through the flexible delivery tube.

13. The method of claim 10, further comprising the steps of:
   directing a cavity-forming device including an expandable member through the flexible delivery tube to the target site within the bone structure with the distal portion of the flexible delivery tube maintaining the curved configuration as the expandable member is directed through the distal portion of the flexible delivery tube; and
   forming a cavity with the expandable member of the cavity-forming device at the target site, wherein the curable material is directed through the flexible delivery tube to within the cavity.

14. The method of claim 10, wherein the distal portion of the flexible delivery tube is formed from a flexible polymer having sufficient columnar strength to maintain a patent longitudinal lumen and the curved configuration against tangential forces from the plurality of elements being directed through the distal portion of the flexible delivery tube.

15. The method of claim 14, wherein an inner diameter of the flexible delivery tube along the distal portion in the curved configuration is greater than outer dimensions of the plurality of elements such that, as the curable material is directed through the distal portion in the curved configuration to the target site, the fluent material backflows through voids between the plurality of elements and the flexible delivery tube to reduce pressurization of the fluent material.

16. The method of claim 10, wherein the flexible delivery tube includes at least one groove extending longitudinally along an outer side of the distal portion in the curved configuration such that, as the curable material is directed through the distal portion in the curved configuration to the target site, the fluent material backflows within the groove to reduce pressurization of the fluent material.

17. The method of claim 10, further comprising the step of directing a pushing device through the flexible delivery tube to direct the curable material through the flexible delivery tube to the target site, wherein the pushing device is flexible to follow the distal portion of the flexible delivery tube maintained the curved configuration.

18. A method for stabilizing a bone structure of a patient with a curable material including a plurality of elements disposed in a fluent material, said method comprising the steps of:
   directing a distal end of an access cannula having a longitudinal axis into the bone structure near a target site;
   positioning a flexible delivery tube through the access cannula such that a distal curved portion of the delivery tube, no longer constrained by the access cannula, assumes a curved configuration within the bone structure with respect to the longitudinal axis of the access cannula; and
   directing the curable material through the flexible delivery tube to the target site with the distal portion of the flexible delivery tube maintaining the curved configuration as the plurality of elements disposed in the fluent material are directed through the distal portion of the flexible delivery tube and wherein the plurality of elements substantially follow a curved path of the bone structure created by the flexible delivery tube.

19. The method of claim 18, further comprising the step of retracting the flexible delivery tube to provide the curved path of the bone structure prior to the step of directing the curable material to follow the curved path.

20. The method of claim 18, further comprising the steps of:
   providing a cavity-forming device comprising an elongate body and an expandable member coupled to the elongate body;
   positioning the expandable member within the curved path of the bone structure distal to the delivery tube at the target site;
   expanding the expandable member to form a cavity; and
   delivering the curable material through the flexible delivery tube and into the cavity.

* * * * *